(12) United States Patent
Otterson et al.

(10) Patent No.: US 9,040,064 B2
(45) Date of Patent: May 26, 2015

(54) LOW-ODOR DIMETHICONE COPOLYOL SULFOSUCCINATE SURFACTANT COMPOSITIONS

(75) Inventors: Richard J. Otterson, Frankfort, IL (US); Kenneth E. Visek, Stickney, IL (US)

(73) Assignee: RHODIA OPERATIONS, Paris (FR)

( * ) Notice: Subject to any disclaimer, the term of this patent is extended or adjusted under 35 U.S.C. 154(b) by 1230 days.

(21) Appl. No.: 12/454,646

(22) Filed: May 21, 2009

(65) Prior Publication Data

US 2009/0234148 A1    Sep. 17, 2009

Related U.S. Application Data

(63) Continuation of application No. 11/372,607, filed on Mar. 10, 2006, now abandoned.

(51) Int. Cl.
*A61K 8/25* (2006.01)
*A61K 8/899* (2006.01)
*A61Q 19/00* (2006.01)
*C08G 77/392* (2006.01)
*C08G 77/46* (2006.01)
*C08L 83/08* (2006.01)

(52) U.S. Cl.
CPC ............... *A61K 8/899* (2013.01); *A61Q 19/00* (2013.01); *C08G 77/392* (2013.01); *C08G 77/46* (2013.01); *C08L 83/08* (2013.01)

(58) Field of Classification Search
CPC ....... A61K 8/899; C08G 77/46; A61Q 19/00; A61Q 5/02; A61Q 5/12
See application file for complete search history.

(56) References Cited

U.S. PATENT DOCUMENTS

| 4,717,498 | A   |   | 1/1988  | Maxon              |         |
|-----------|-----|---|---------|--------------------|---------|
| 4,849,127 | A   | * | 7/1989  | Maxon              | 510/537 |
| 5,118,764 | A   |   | 6/1992  | Ichinohe et al.    |         |
| 5,225,509 | A   |   | 7/1993  | Heinrich et al.    |         |
| 5,696,192 | A   |   | 12/1997 | Harashima          |         |
| 6,784,271 | B2  |   | 8/2004  | Nakanishi          |         |

OTHER PUBLICATIONS

Product data sheet of Dow Corning 193 Surfactant (dimethicone copolyl with PEG-12 as the R group).*

* cited by examiner

*Primary Examiner* — David J Blanchard
*Assistant Examiner* — Tigabu Kassa

(57) ABSTRACT

Dimethicone copolyol sulfosuccinate surfactant compounds having low-odor characteriztics are disclosed. The low-odor dimethicone copolyol sulfosuccinate is substantially free from propionaldehyde and acid-releasable precursors of propionaldehyde, thereby substantially eliminating the cosmetically undesirable odor characteriztic of conventional dimethicone copolyol sulfosuccinate surfactants. The low-odor dimethicone copolyol sulfosuccinates are suitable for use as surfactants in household or personal care products and applications.

18 Claims, No Drawings

LOW-ODOR DIMETHICONE COPOLYOL SULFOSUCCINATE SURFACTANT COMPOSITIONS

CROSS-REFERENCE TO RELATED APPLICATIONS

This application is a continuation of U.S. application Ser. No. 11/372,607, filed on Mar. 10, 2006, now abandoned which is incorporated herein by reference.

FIELD OF THE INVENTION

This invention relates to sulfosuccinate surfactants. More particularly, this invention relates to silicone-based sulfosuccinate surfactants having low-odor characteristics.

BACKGROUND OF THE INVENTION

Sulfosuccinate surfactants have been used in the cosmetic industry primarily to improve the mildness of skin cleansers, shampoos and other personal care products. Such surfactants are usually diesters or monoesters, with the monoester being preferred because of its mildness and foam enhancement properties. Prior to the development of dimethicone copolyol sulfosuccinates, which are disclosed in U.S. Pat. No. 4,717,498 to Maxon, which is incorporated herein by reference, primarily two half ester or monoester derivatives had been used for shampoos. Such derivatives included derivatives of monoalcohol amides, such as oleamide MEA, oleamide IPA and undecylenamide MEA, and derivatives of fatty alcohols and ethoxylated alcohols, such as lauryl, laureth and oleyl alcohols.

The sulfosuccinates obtained from diesters and monoesters vary considerably in their foaming, viscosity building, solubility and conditioning properties. In general, they are gentle to the skin and eyes when compared to high foaming surfactants, and are usually blended with such high foaming surfactants to obtain compositions that exhibit some degree of both mildness and foaming properties. Dimethicone copolyol sulfosuccinates, on the other hand, have useful foaming characteristics, while also being quite mild to the skin. One factor which has limited the use of dimethicone copolyol sulfosuccinates in cosmetics is that such surfactants typically exhibit a characteristic odor, which can be objectionable in some personal care and cosmetic products.

There is an ongoing need, therefore, for dimethicone copolyol sulfosuccinate surfactants that have relatively low-odor characteristics suitable for use in cosmetic applications. The present invention fulfills this need.

SUMMARY OF THE INVENTION

The present invention provides low-odor compositions including a dimethicone copolyol sulfosuccinate having a dimethicone copolyol portion and a sulfosuccinate portion. The low-odor compositions of the present invention include a dimethicone copolyol sulfosuccinate of the formula:

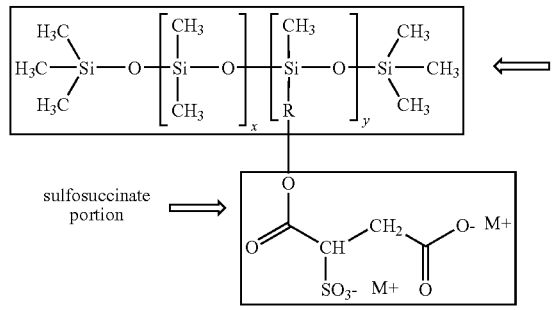

wherein R is a polymer of ethylene oxide, a polymer of propylene oxide, a polymer of butylene oxide, a polymer of tetrahydrofuran, a polymer of glycerol, or a copolymer of two or more monomers selected from the group consisting of ethylene oxide, propylene oxide, butylene oxide, tetrahydrofuran, and glycerol; M+ is an alkali (Group IA) metal cation (e.g., sodium, potassium or lithium) or an ammonium group; x has a value in the range of 0 to about 100; and y has a value in the range of 1 to about 100. Preferably, the compound has an equivalent weight in the range of about 400 to about 3000 grams per equivalent, wherein the term "equivalent weight" refers to the average molecular weight (i.e., grams of compound per mole) divided by the number of moles of alkoxylated monomer units (i.e., the value of "y") in the molecule.

Preferably, R is a polyoxyalkylene moiety selected from the group consisting of:
—$(C_2H_4O)_s$—$C_2H_4$—;
—$(C_3H_6O)_t$—$C_3H_6$—; and
—$(C_2H_4O)_v$—$(C_3H_6O)_w$—Y—;

wherein s and t each independently have a value in the range of 2 to about 30; v and w each independently have a value in the range of 1 to about 30; and Y is $C_2H_4$ or $C_3H_6$. The $C_3H_6$ and $C_3H_6O$ moieties can be linear or branched, preferably branched. The —$(C_2H_4O)_v$—$(C_3H_6O)_w$—Y— group can be a block copolymer, a random copolymer or an alternating copolymer of $C_2H_4O$ and $C_3H_6O$ moieties.

The dimethicone copolyol portion of the dimethicone copolyol sulfosuccinate can have any hydrophilic/lipophilic balance (HLB), as calculated by methods well known in the art. Preferably, the dimethicone copolyol portion of the dimethicone copolyol sulfosuccinate has a calculated HLB value in the range of about 10 to about 17.

It has been found that the sensory, cosmetically undesirable, odor characteristic of prior art dimethicone copolyol compositions is primarily due to propionaldehyde present in the surfactant composition or released from the surfactant composition under acidic conditions. The low-odor dimethicone copolyol compositions of the present invention are substantially free from propionaldehyde and acid-releasable precursors thereof, such as propionaldehyde enol ethers, which affords a cosmetically acceptable, suitably low-odor sensory characteristic to the composition.

A variation of the composition of the dimethicone copolyol sulfosuccinate surfactants of the present invention is represented by the formula:

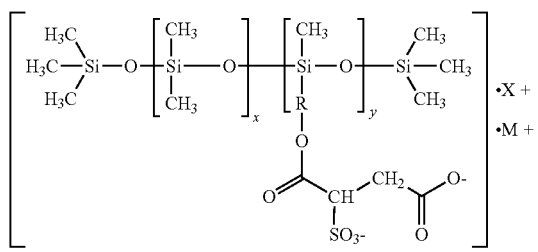

wherein X+ is an ammonium group derived from an amino alcohol, preferably derived from an amino alcohol selected from the group consisting of monoethanolamine, diethanolamine, triethanolamine, monoisopropanolamine and diglycolamine; while M+, R, x, and y are as defined above.

Another variation of the sulfosuccinate surfactant of the present invention is represented by the formula:

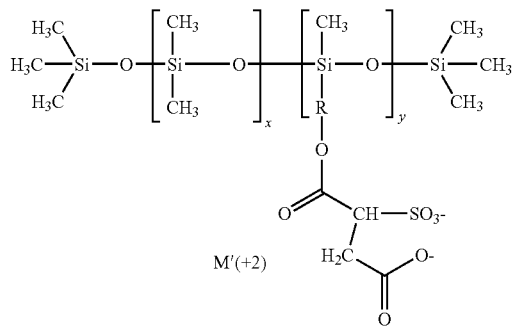

wherein M'(+2) is an alkaline earth (Group II) cation, for example, calcium, magnesium or barium, rather than an alkali metal cation; while R, x, and y are as defined above.

Yet another form of the sulfosuccinate surfactant of the present invention is represented by the following formula:

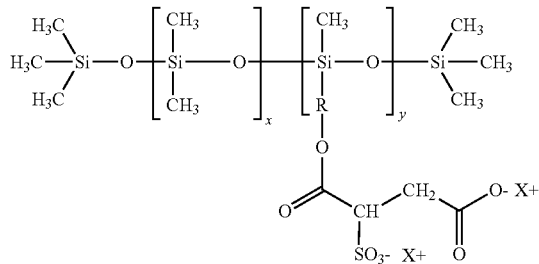

wherein X+, R, x, and y are as defined above. Typically, the ammonium group, X+, is obtained from a sulfite salt containing an amino alcohol.

The compositions of the present invention are preferably prepared by reacting the ethoxylated polyether side chains of a low-odor dimethicone copolyol with maleic anhydride to form a monoester, and then converting the monoester to a sulfosuccinate by sulfonation of the double bond with a metallic or amino alcohol sulfite. The dimethicone copolyol starting material utilized in the reaction is preferably substantially free from propionaldehyde and acid-releasable precursors thereof, such as propionaldehyde enol ethers. Metallic sulfite and amino salts can also be used either alone or in combination for sulfonation of the double bond. The resulting sulfosuccinate is a silicone-based surfactant, which exhibits mildness to the skin, excellent foam stabilizing properties, and has a low-odor characteristic suitable for use in household or personal care products and applications.

DETAILED DESCRIPTION OF PREFERRED EMBODIMENTS

The term "low-odor dimethicone copolyol" refers herein to dimethicone copolyol type compounds that are substantially free of propionaldehyde and acid-releasable precursors of propionaldehyde. The term "low-odor" as applied to surfactant compositions of this invention means that the discernible sensory odor characteristic of the composition is improved, and deemed cosmetically desirable, relative to the discernible odor of a counterpart composition having a relatively high content of propionaldehyde, or acid precursors thereof (e.g., greater than about 3200 ppm).

The dimethicone copolyol sulfosuccinate compositions of the present invention preferably are prepared by reacting the ethoxylated polyether side chains of a dimethicone copolyol with maleic anhydride to form a monoester. The side chains involved in this reaction are a polymer or copolymer of ethylene oxide, propylene oxide, butylene oxide, tetrahydrofuran, and/or glycerol. Preferably, the side chains involved in this reaction are a polymer or copolymer of ethylene oxide and/or propylene oxide. The dimethicone copolyol preferably is substantially free of propionaldehyde and acid-releasable precursors thereof. The condensation reaction with maleic anhydride is represented by the following equation.

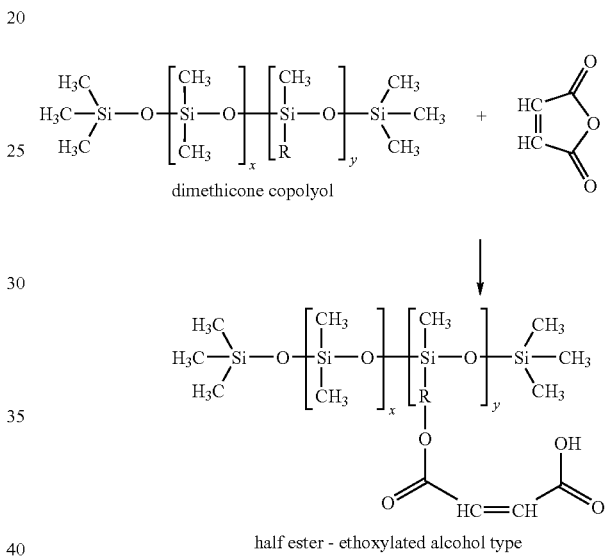

half ester - ethoxylated alcohol type

In the above equation, the R group side chains are polymers or copolymers ethylene oxide, propylene oxide, butylene oxide, tetrahydrofuran, and/or glycerol, with the preferred R group being selected from the group consisting of:

—(C$_2$H$_4$O)$_s$—C$_2$H$_4$—;
—(C$_3$H$_6$O)$_t$—C$_3$H$_6$—; and
—(C$_2$H$_4$O)$_v$—(C$_3$H$_6$O)$_w$—Y—;

wherein s and t each independently have a value in the range of 2 to about 30; v and w each independently have a value in the range of 1 to about 30; and Y is C$_2$H$_4$ or C$_3$H$_6$. In the dimethicone copolyol sulfosuccinate surfactants of the present invention, the C$_3$H$_6$ and C$_3$H$_6$O moieties can be linear or branched, preferably branched. The —(C$_2$H$_4$O)$_v$—(C$_3$H$_6$O)$_w$—Y— group can be a block copolymer, a random copolymer or an alternating copolymer of C$_2$H$_4$O and C$_3$H$_6$O moieties.

Preferably, x has a value in the range of 0 to about 100 and y has a value in the range of 1 to about 100. More preferably, x has a value in the range of 1 to about 50, and y has a value in the range of 1 to about 50. The values of x, y, s, t, v and w preferably are selected to produce a dimethicone copolyol sulfosuccinate product with an equivalent weight in the range of about 400 to about 3000 grams per equivalent. Preferably, the dimethicone copolyol portion of the compound has a calculated HLB value in the range of about 10 to about 17.

The low odor dimethicone copolyol sulfosuccinate surfactants of the invention can be random copolymers, block copolymers or alternating copolymers (i.e., the "x" and "y" monomer units can be randomly distributed, arranged in blocks, or arranged in repeating or alternating patterns).

The low-odor compositions of the present invention are substantially free from propionaldehyde and acid-releasable precursors thereof, such as propionaldehyde enol ethers. Examples of acid-releasable propionaldehyde precursors include, without limitation, an enol ether of propionaldehyde, such as a compound of Formula (I):

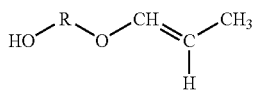

wherein R is
—$(C_2H_4O)_s$—$C_2H_4$—;
—$(C_3H_6O)_t$—$C_3H_6$—; or
—$(C_2H_4O)_v$—$(C_3H_6O)_w$—Y—;
wherein s and t each independently have a value in the range of 2 to about 30; v and w each independently have a value in the range of 1 to about 30; and Y is $C_2H_4$ or $C_3H_6$. The $C_3H_6$ and $C_3H_6O$ moieties can be linear or branched, preferably branched. The —$(C_2H_4O)_v$—$(C_3H_6O)_w$—Y— group can be a block copolymer, a random copolymer or an alternating copolymer of $C_2H_4O$ and $C_3H_6O$ moieties.

Dimethicone copolyol sulfosuccinate compositions of the present invention can be prepared by condensation of a low-odor dimethicone copolyol with maleic anhydride to form a monoester with at least one R group in the dimethicone copolyol molecule, preferably with a majority of the R groups, and more preferably with each R group in the molecule. The olefinic bond in the maleic monoester is then sulfonated to afford the sulfosuccinate.

A preferred condensation reaction proceeds by reacting about 1 to about 1.3 moles of maleic anhydride with about 1 equivalent of a dimethicone copolyol. The dimethicone copolyol is heated to a temperature in the range of about 45 to about 70° C., with the preferred temperature being in the range of about 60 to about 65° C. Preferably, the dimethicone copolyol is substantially free of propionaldehyde and acid-releasable precursors of propionaldehyde, such as an enol ether precursor of propionaldehyde (e.g., a compound of Formula (I), and the like). The maleic anhydride can be dissolved in an aprotic solvent (e.g., tetrahydrofuran, dioxane, glyme, diglyme, a chlorinated hydrocarbon such as dichloromethane, and the like), if desired, or can be utilized without added solvent. The reaction mixture of dimethicone copolyol and maleic anhydride is maintained at a temperature in the range of about 40 to about 70° C., preferably about 50 to about 65° C. under conditions and according to practices known to those skilled in the art until a constant acid value or number is obtained.

The resulting maleic monoester of dimethicone copolyol is then converted into a sulfosuccinate surfactant of the present invention by sulfonating the double bond of the maleic monoester with a metallic sulfite salt, ammonium sulfite, an amine sulfite salt, or a combination thereof. The preferred conversion is accomplished by reacting the olefinic bond of the maleic anhydride portion of the dimethicone copolyol monoester with approximately equal molar amount of an alkali metal sulfite in an aqueous solution in the following manner:

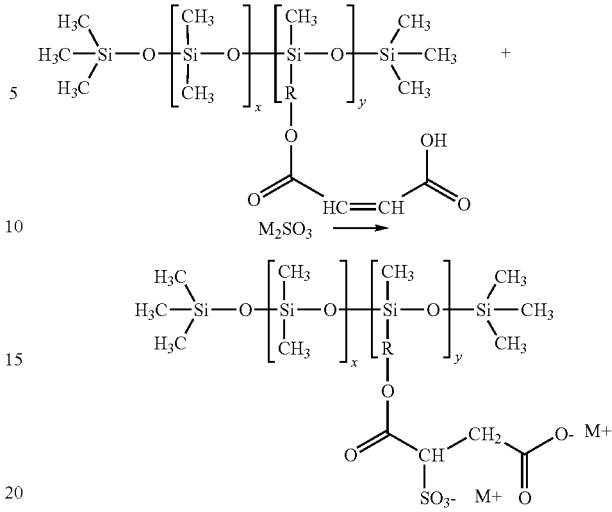

wherein M+ is an alkali (Group IA) metal cation, for example, sodium, potassium or lithium, or ammonium group, while R, x and y are as defined above.

The alkali metal sulfite preferably is dissolved in water at a temperature of about 40 to about 60° C., more preferably about 40 to about 50° C. After the alkali metal sulfite is thoroughly dissolved, the maleic monoester of dimethicone copolyol is added to the solution while maintaining the reaction mixture in a fluid state. The mixture is allowed to react for approximately one half hour to about three hours, or until the concentration of the free alkali metal sulfite is about 3% or less, with the preferred concentration being less than about 1%.

In another embodiment, the conversion of the maleic monoester of dimethicone copolyol to a sulfosuccinate is accomplished by using compounds other than, or in addition to, alkali metal or ammonium sulfite salts. Specifically, an alkali metal or ammonium sulfite in conjunction with an amino alcohol can be used to sulfonate the double bond of the monoester. These sulfosuccinates can be prepared in the following manner:

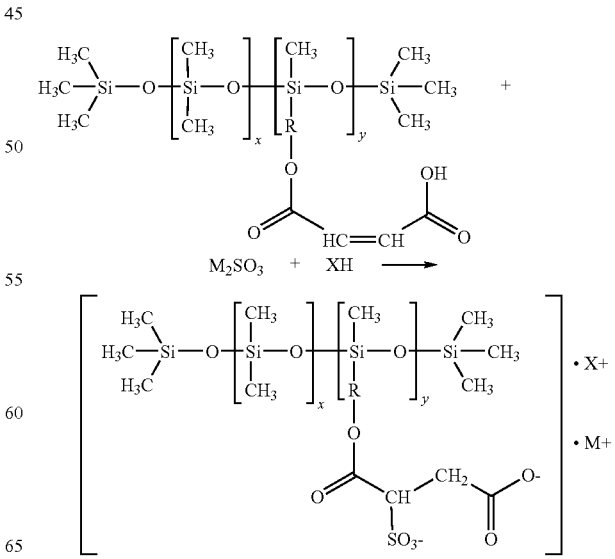

wherein M+ is an alkali metal cation or ammonium group and X+ is an ammonium group derived from an amine(XH), preferably an amino alcohol such as an amine ethoxylate or an amine propoxylate, while R, x, and y are as defined above. Preferably, the ammonium group, X+, is derived from an amine selected from the group consisting of monoethanolamine, diethanolamine, triethanolamine, monoisopropanolamine, diglycolamine, an ethoxylate thereof, and a propoxylate thereof.

Alkaline earth sulfites also can be used in place of alkali metal sulfites or ammonium sulfite to convert the maleic monoester of dimethicone copolyol to a sulfosuccinate. When used alone, the conversion reaction occurs in the following manner:

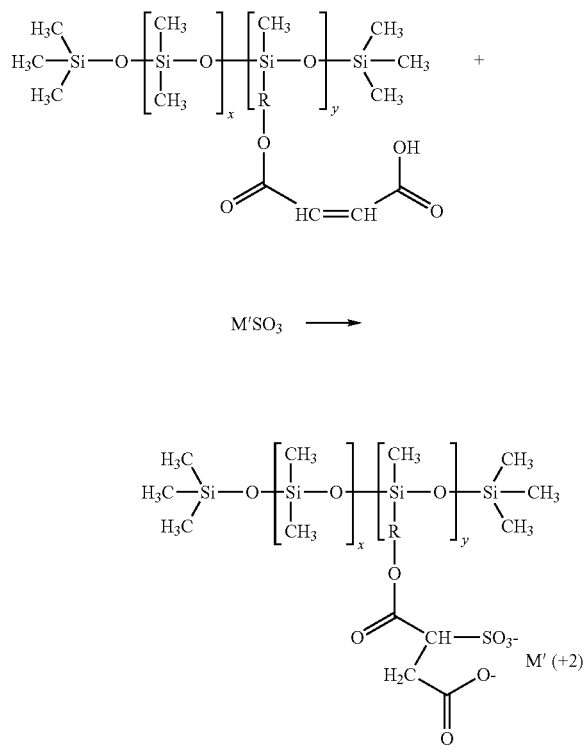

wherein M'(+2) is an alkaline earth (Group II) metal cation, for example, calcium, magnesium or barium, while R, x and y are as defined above.

Amino sulfites also can be used without the metallic sulfites to convert the maleic monoester of dimethicone copolyol to a sulfosuccinate. When used alone, the conversion reaction occurs as follows:

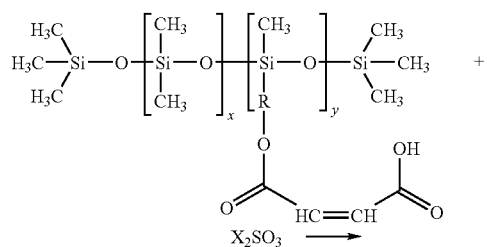

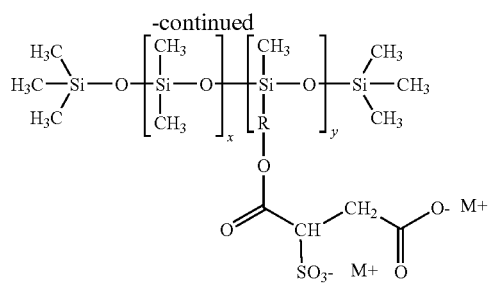

wherein X+ is an ammonium group derived from an amine, preferably an amino alcohol such as an amine ethoxylate and/or an amine propoxylate, more preferably an amino alcohol selected from the group consisting of monoethanolamine, diethanolamine, triethanolamine, monoisopropanolamine or diglycolamine, while R, x and y are as defined above.

The values for x and y in many commercial dimethicone copolyol compounds that can be used to produce the compositions of the present invention cannot be readily determined, because such values generally are kept as trade secrets and are not released or made public by the commercial manufacturers of dimethicone copolyols. However, non-limiting examples of commercial dimethicone copolyol compounds, which reportedly have a low-odor characteristic, suitable for preparing a low-odor dimethicone copolyol sulfosuccinate composition of the present invention include a purified version of DOW CORNING® 193 surfactant manufactured by the Dow Corning Corporation, Midland, Mich., and SILSURF® D212-CG, manufactured by Siltech Corporation. A particularly preferred dimethicone copolyol suitable for preparing a dimethicone copolyol sulfosuccinate composition of the invention is DOW CORNING® UP-1005 Ultra Pure Fluid (INCI Name: PEG-12 Dimethicone), manufactured by the Dow Corning Corporation, which is substantially free from propionaldehyde and acid-releasable precursors thereof, such as enol ethers of Formula (I) as described above.

Preparation of low-odor dimethicone copolyol type compounds that are reportedly substantially free of propionaldehyde and acid-releasable precursors of propionaldehyde are disclosed in U.S. Pat. No. 5,118,764 to Ichinohe et al.; U.S. Pat. No. 5,225,509 to Heinrich et al.; U.S. Pat. No. 5,696,192 to Harashima; U.S. Pat. No. 5,869,727 to Crane et al.; U.S. Pat. No. 6,162,888 to Lee et al.; U.S. Pat. No. 6,437,162 to O'Lenick, Jr.; and U.S. Pat. No. 6,784,271 to Nakanishi.

Preferred dimethicone copolyol compounds used to prepare the low-odor surfactant compositions of the present invention desirably possess the following characteristics: the dimethicone copolyol should have an equivalent weight in the range of about 350 to about 1100 grams per equivalent and should be essentially free from any extraneous solvents, propionaldehyde, and acid-releasable precursors of propionaldehyde (i.e., compounds that release propionaldehyde under acidic conditions). Preferably the dimethicone copolyol is substantially free from enol ethers of Formula (I).

Preferably, the hydroxyl number of the dimethicone copolyol is in the range of about 20 to about 160, more preferably in the range of about 60 to about 100, most preferably in the range of about 70 to about 90. If the hydroxyl number of the dimethicone copolyol is too low, the amount of the other reactants (maleic anhydride and bisulfite compounds) will be insufficient to react properly, and the resulting product will have either slight or no differences in properties from the original dimethicone copolyol. If extraneous solvents are present in too large amounts, such solvents interfere with the reaction to the extent that limited reaction can occur or the reaction can be partially blocked. The resulting product then will not possess the desired characteristics of a low-odor surfactant with useful foaming ability and which is mild to the skin.

The dimethicone copolyol starting materials can have any HLB value. Preferably, the dimethicone copolyol starting material has a calculated HLB in the range of about 10 to about 17. The HLB represents a ratio of the silicone portion of the compound to the ethoxylated side chain portion of the compound (i.e., the R groups).

Diester dimethicone copolyol sulfosuccinates can also be prepared by reacting about 1 mole of the diester with about 1 molar equivalent of the metallic bisulfite or amine bisulfite.

Several tests have been conducted using some representative compositions of the present invention to verify the low-odor characteristics of some of the compositions of the present invention.

Each composition was prepared using the process described earlier by which about 1 equivalent of dimethicone copolyol was reacted with about 1 to about 1.3 moles of maleic anhydride, i.e., as described in detail in U.S. Pat. No. 4,717,498 to Maxon, incorporated herein by reference. For example, a low-odor dimethicone copolyol sulfosuccinate surfactant was prepared from DOW CORNING® UP-1005, and compared with a conventional dimethicone copolyol sulfosuccinate surfactant prepared from standard, commercial DOW CORNING® 193, which had a detectable propionaldehyde odor.

As used herein, the term "substantially free from", when used in reference to propionaldehyde and acid-releasable precursors thereof means a level of propionaldehyde in the head space above a liquid sample of the product that is low enough to be essentially free of objectionable odor sensorially discernible to a human observer. For example, in one test, dimethicone copolyol sulfosuccinate surfactant of this invention prepared from DOW CORNING® UP-1005 was substantially free of objectionable odor and had a head space concentration of propionaldehyde of about 16 parts per million (ppm) as determined by head-space gas chromatography. By comparison, conventional dimethicone copolyol sulfosuccinate surfactant prepared with the typical, non-purified commercial dimethicone copolyol product, DOW CORNING® 193, had propionaldehyde levels in the range of about 2000 to about 4500 ppm and had readily discernible, objectionable propionaldehyde odors. Similarly, the calculated propionaldehyde enol ether content (weight percent) of the dimethicone copolyol sulfosuccinate prepared from DOW CORNING® UP-1005 was about zero, compared to about 10 weight percent for the dimethicone copolyol sulfosuccinate prepared from non-purified DOW CORNING® 193.

Another aspect of this invention is a household or personal care product comprising at least one low-odor composition of the invention in a physiologically tolerable (e.g. non-toxic, mild to the skin, non-allergenic, and the like) vehicle well known in the cosmetic and personal care arts. The compositions and products can also include other additives and adjuvants suitable for use in cosmetics and personal care products. Non-limiting examples of vehicles, additives and adjuvants suitable for use in household and personal care products can be found in numerous technical publications and supplier's literature, such as in any edition of the well known *International Cosmetic Ingredient Dictionary and Handbook (INCI)*, published by the Cosmetic, Toiletry, and Fragrance Association, Inc., Wash., D.C., relevant portions of which are incorporated herein by reference. Exemplary household and personal care products, without limitation, include cosmetics, hair and skin care products, such as cleansers, conditioners, moisturizers, and the like, oral and personal hygiene products, and household products, such as cleaners. which come in contact with the skin of the user.

The compositions described herein are intended to illustrate embodiments of the invention and do not limit the scope of the invention, which is defined by the appended claims. Alternatives to and equivalents of the specific embodiments described can be made and considered to be within the scope of the invention as defined by the claims.

We claim:

1. A low-odor composition that is substantially free from propionaldehyde and acid-releasable precursors of propionaldehyde and suitable for use in cosmetic and personal care applications, the composition comprising a dimethicone copolyol sulfosuccinate produced by the steps of:
   reacting a dimethicone copolyol with maleic anhydride to form a maleic monoester, the dimethicone copolyol being substantially free of propionaldehyde and acid-releasable precursors of propionaldehyde; and
   sulfonating the maleic monoester with a compound selected from the group consisting of an alkali metal sulfite, an alkaline earth sulfite, ammonium sulfite, an amino sulfite, and a combination of any of the foregoing with an amino alcohol.

2. The composition of claim 1 wherein the dimethicone copolyol has an equivalent weight in the range of about 350 to about 1100 grams per equivalent.

3. The composition of claim 2 wherein the dimethicone copolyol has a calculated HLB value in the range of about 10 to about 17.

4. The composition of claim 1 wherein the composition contains less than 3200 parts per million of propionaldehyde and acid-releasable precursors of propionaldehyde, and is free of objectionable odor sensorially discernible to a human observer compared to that of a counterpart composition containing greater than 3200 parts of parts per million of propionaldehyde and acid-releasable precursors of propionaldehyde.

5. The composition of claim 1 wherein the dimethicone copolyol sulfosuccinate has the formula:

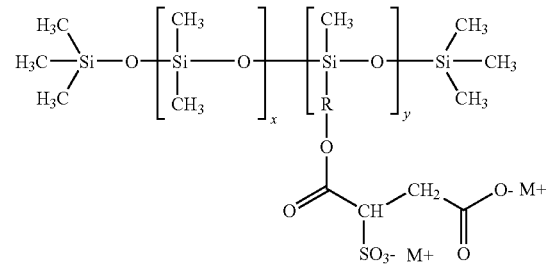

wherein the composition is substantially free of propionaldehyde and acid-releasable precursors of propionaldehyde; R is a polymer of ethylene oxide, a polymer of propylene oxide, a polymer of butylene oxide, a polymer of tetrahydrofuran, a polymer of glycerol, or a copolymer of two or more monomers selected from the group consisting of ethylene oxide, propylene oxide, butylene oxide, tetrahydrofuran, and glycerol; M+ is an alkali metal cation or ammonium group; x has a value in the range of 0 to about 100 and y has a value in the range of 1 to about 100.

6. The composition of claim 5 wherein R is selected from the group consisting of:

—(C$_2$H$_4$O)$_s$—C$_2$H$_4$—;
—(C$_3$H$_6$O)$_t$—C$_3$H$_6$—; and
—(C$_2$H$_4$O)$_v$—(C$_3$H$_6$O)$_w$—Y—;

wherein s and t each independently have a value in the range of 2 to about 30; v and w each independently have a value in the range of 1 to about 30; and Y is C$_2$H$_4$ or C$_3$H$_6$.

7. The composition of claim 5 wherein the composition contains less than 3200 parts per million of propionaldehyde and acid-releasable precursors of propionaldehyde, and is free of objectionable odor sensorially discernible to a human observer compared to that of a counterpart composition containing greater than 3200 parts of parts per million of propionaldehyde and acid-releasable precursors of propionaldehyde.

8. The composition of claim 1 wherein the dimethicone copolyol sulfosuccinate has the formula:

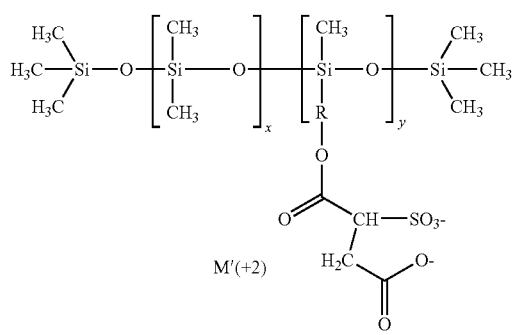

wherein the composition is substantially free of propionaldehyde and acid-releasable precursors of propionaldehyde; R is a polymer of ethylene oxide, a polymer of propylene oxide, a polymer of butylene oxide, a polymer of tetrahydrofuran, a polymer of glycerol, or a copolymer of two or more monomers selected from the group consisting of ethylene oxide, propylene oxide, butylene oxide, tetrahydrofuran, and glycerol; M'(+2) is an alkaline earth metal cation; x has a value in the range of 0 to about 100 and y has a value in the range of 1 to about 100.

9. The composition of claim 8 wherein R is selected from the group consisting of:

—(C$_2$H$_4$O)$_s$—C$_2$H$_4$—;
—(C$_3$H$_6$O)$_t$—C$_3$H$_6$—; and
—(C$_2$H$_4$O)$_v$—(C$_3$H$_6$O)$_w$—Y—;

wherein s and t each independently have a value in the range of 2 to about 30; v and w each independently have a value in the range of 1 to about 30; and Y is C$_2$H$_4$ or C$_3$H$_6$.

10. The composition of claim 8 wherein the composition contains less than 3200 parts per million of propionaldehyde and acid-releasable precursors of propionaldehyde, and is free of objectionable odor sensorially discernible to a human observer compared to that of a counterpart composition containing greater than 3200 parts of parts per million of propionaldehyde and acid-releasable precursors of propionaldehyde.

11. The composition of claim 1 wherein the dimethicone copolyol sulfosuccinate has the formula:

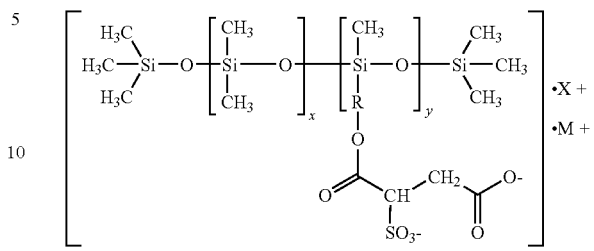

wherein the composition is substantially free of propionaldehyde and acid-releasable precursors of propionaldehyde; X+ is an ammonium group derived from an amino alcohol, an amine ethoxylate or an amine propoxylate; R is a polymer of ethylene oxide, a polymer of propylene oxide, a polymer of butylene oxide, a polymer of tetrahydrofuran, a polymer of glycerol, or a copolymer of two or more monomers selected from the group consisting of ethylene oxide, propylene oxide, butylene oxide, tetrahydrofuran, and glycerol; M+ is an alkali metal cation or ammonium group; x has a value in the range of 0 to about 100 and y has a value in the range of 1 to about 100.

12. The composition of claim 11 wherein the ammonium group, X+, is derived from at least one amine selected from the group consisting of monoethanolamine, diethanolamine, triethanolamine, monoisopropanolamine and diglycolamine.

13. The composition of claim 11 wherein R is selected from the group consisting of:

—(C$_2$H$_4$O)$_s$—C$_2$H$_4$—;
—(C$_3$H$_6$O)$_t$—C$_3$H$_6$—; and
—(C$_2$H$_4$O)$_v$—(C$_3$H$_6$O)$_w$—Y—;

wherein s and t each independently have a value in the range of 2 to about 30; v and w each independently have a value in the range of 1 to about 30; and Y is C$_2$H$_4$ or C$_3$H$_6$.

14. The composition of claim 11 wherein the composition contains less than 3200 parts per million of propionaldehyde and acid-releasable precursors of propionaldehyde, and is free of objectionable odor sensorially discernible to a human observer compared to that of a counterpart composition containing greater than 3200 parts of parts per million of propionaldehyde and acid-releasable precursors of propionaldehyde.

15. The composition of claim 1 wherein the dimethicone copolyol sulfosuccinate has the formula:

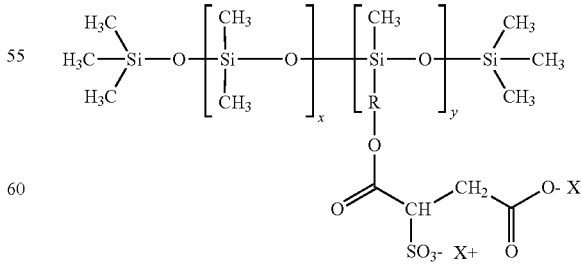

wherein the composition is substantially free of propionaldehyde and acid-releasable precursors of propionaldehyde; X+ is an ammonium group derived from an amino alcohol, an amine ethoxylate or an amine propoxylate; R is a polymer of ethylene oxide, a polymer of propylene oxide, a polymer of butylene oxide, a polymer of tetrahydrofuran, a polymer of glycerol, or a copolymer of two or more monomers selected from the group consisting of ethylene oxide, propylene oxide, butylene oxide, tetrahydrofuran, and glycerol; x has a value in the range of 0 to about 100 and y has a value in the range of 1 to about 100.

16. The composition of claim 15 wherein the ammonium group, X+, is derived from at least one amine selected from the group consisting of monoethanolamine, diethanolamine, triethanolamine, monoisopropanolamine and diglycolamine.

17. The composition of claim 15 wherein R is selected from the group consisting of:
—$(C_2H_4O)_s$—$C_2H_4$—;
—$(C_3H_6O)_t$—$C_3H_6$—; and
—$(C_2H_4O)_v$—$(C_3H_6O)_w$—Y—;
wherein s and t each independently have a value in the range of 2 to about 30; v and w each independently have a value in the range of 1 to about 30; and Y is $C_2H_4$ or $C_3H_6$.

18. The composition of claim 15 wherein the composition contains less than 3200 parts per million of propionaldehyde and acid-releasable precursors of propionaldehyde, and is free of objectionable odor sensorially discernible to a human observer compared to that of a counterpart composition containing greater than 3200 parts of parts per million of propionaldehyde and acid-releasable precursors of propionaldehyde.

\* \* \* \* \*